US006251646B1

(12) United States Patent
Dicosimo et al.

(10) Patent No.: US 6,251,646 B1
(45) Date of Patent: Jun. 26, 2001

(54) METHOD FOR STABILIZING NITRILASE ACTIVITY AND PRESERVING MICROBIAL CELLS

(75) Inventors: Robert Dicosimo, Rockland; Arie Ben-Bassat, Newark, both of DE (US); Robert D. Fallon, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/352,015

(22) Filed: Jul. 12, 1999

(51) Int. Cl.$^7$ ............... C12N 9/00; C12N 9/96; C12N 11/04; C12N 11/00; C12N 1/04
(52) U.S. Cl. .............. 435/183; 435/182; 435/188; 435/177; 435/174; 435/260; 435/252.1
(58) Field of Search .................... 435/260, 174, 435/183, 177, 182, 188, 252.1

(56) References Cited

U.S. PATENT DOCUMENTS

| 4,343,900 | 8/1982 | Watanabe | 435/129 |
|---|---|---|---|
| 4,900,672 | 2/1990 | Yamanda et al. | 435/188 |
| 4,931,391 | 6/1990 | Enomoto et al. | 435/188 |
| 5,629,190 | 5/1997 | Petre et al. | 435/227 |
| 5,635,391 | 6/1997 | Petre et al. | 435/252 |
| 5,705,382 | 1/1998 | Endo et al. | 435/260 |
| 5,814,508 | * 9/1998 | Di Cosimo et al. | 435/227 |

FOREIGN PATENT DOCUMENTS 0 707 061   4/1996   (EP) .

10042885   2/1998   (JP) ................ C12P/13/02

OTHER PUBLICATIONS

Kobayashi et al., FEMS Microbiol. Lett., 217–234, 1994.
Kobayashi et al., Tetrahedron , 46, 5587–5590, 1990.
Kobayashi et al., J. Bacteriology, 172, 4807–4815, 1990.
Levy–Schil et al., Gene 161, 15–20, 1995.
Gradley et al., Biotechnology Lett. 16, 41–46, 1994.
Bengis–Garber et al., Appl. Microbiol. Biotechnol., 32,11–16, 1989.
Kobayashi et al., Eur. J. Biochem.182, 349–356, 1989.

* cited by examiner

*Primary Examiner*—Eggerton A. Campbell
*Assistant Examiner*—Joyce Tung

(57) ABSTRACT

A method for the stabilization of nitrilase activity of unimmobilized or immobilized microbial cells has been developed. The unimmobilized or immobilized microbial cells are stored in an aqueous solution containing from 0.100 M to the saturation concentration of an inorganic salt of bicarbonate or carbonate, including ammonium, sodium and potassium salts of bicarbonate or carbonate. Aqueous suspensions containing at least 100 mM bicarbonate or carbonate limit microbial contamination of the stored enzyme catalyst, as well as stabilize the desired nitrilase activity of the unimmobilized or immobilized cells. Microorganisms which are characterized by an nitrilase activity and are stabilized and preserved by this method include *Acidovorax facilis* 72-PF-15 (ATCC 55747), *Acidovorax facilis* 72-PF-17 (ATCC 55745), and *Acidovorax facilis* 72W (ATCC 55746).

8 Claims, No Drawings

METHOD FOR STABILIZING NITRILASE ACTIVITY AND PRESERVING MICROBIAL CELLS

FIELD OF THE INVENTION

The present invention relates to the field of microbiology and molecular biology. More specifically, a method has been developed to stabilize the nitrilase activity of unimmobilized or immobilized cells and to preserve the integrity of the microbial cells, where the unimmobilized or immobilized cells are stored in an aqueous solution containing from 0.100 M to the saturation concentration of an inorganic salt of bicarbonate or carbonate, including ammonium, sodium, and potassium salts of bicarbonate or carbonate.

BACKGROUND OF THE INVENTION

The occurrence of nitrile hydrolyzing enzymes has been widely described. Within this family of enzymes, two broad classes are generally recognized. The first includes the nitrile hydratases which catalyze the addition of one molecule of water to the nitrile, resulting in formation of the corresponding amide:

Reaction 1

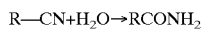

R—CN+$H_2$O→RCON$H_2$

The second group includes the nitrilases which catalyze adding two molecules of water to the nitrile resulting in the direct formation of the corrsponding carboxylic acid plus ammonia, without the intermediate formation of the corresponding amide:

Reaction 2

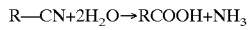

R—CN+2$H_2$O→RCOOH+N$H_3$

Cells containing aromatic or aliphatic nitrilases have been used to directly convert a nitrile to the corresponding carboxylic acid ammonium salt in aqueous solution without the intermediate formation of an amide (Kobayashi et al., *FEMS Microbiol. Lett.* 120:217–234 (1994)). Cells having nitrilase activity include *Rhodococcus rhodochrous* K22 (Kobayashi et al., *Tetrahedron* 46:5587–5590 (1990); Kobayashi et al., *J. Bacteriology* 172:4807–4815 (1990)), *Comamonas testosteroni* (U.S. Pat. Nos. 5,629,190 and 5,635,391; Lévy-Schil et al., *Gene* 161:15–20 (1995)), *Rhodococcus rhodochrous* NCIMB 11216 (Gradley et al., *Biotechnology Lett.* 16:41–46 (1994); Bengis-Garber et al., *Appl. Microbiol. Biotechnol.* 32:11–16 (1989)), and *Rhodococcus rhodochrous* J1 (Kobayashi et al., *Eur. J Biochem.* 182:349–356 (1989)). Of those nitrilases that have been sequenced, a unique conserved active-site cysteine has been identified as the functional group responsible for enzymatic nitrile hydration (Lévy-Schil et al., *Gene* 161:15–20 (1995)). The typical method for stabilizing the cysteine-catalyzed nitrilase activity has been to include mM concentrations of dithiothreitol (DTT) and/or ethylenediaminetetraacetic acid (EDTA) in the aqueous buffer containing the isolated enzyme or whole cell.

A method for preserving suspensions of cells or immobilized cells has been described in EP 0707061 A1, where the storage solution contains at least one inorganic salt selected from the group consisting of phosphates, borates, sulfates, sulfites, and hydrochlorides. Types of salts included sodium, potassium, and ammonium salts. The concentration of these salts ranged from 100 mM to the saturation concentration of the inorganic salt. The use of these inorganic salts to preserve the nitrilase activity of *Gordona terrae* MA-1 was demonstrated. Japanese patent application JP 10042885 A2 describes the production of amides and/or organic acids by treating nitriles with culture media, cells, cell preparations, enzymes, or enzyme preparations from microorganisms having nitrile-hydrolyzing activities in aqueous reaction mixture containing $H_2CO_3$ or carbonate salts, where the inclusion of $H_2CO_3$ or carbonate salts is reported to increase the observed activity of the nitrile-hydrolyzing enzyme towards the nitrile; no disclosure of an improvement in the stability of the nitrile-hydrolyzing activity of the cells over time when stored was made.

Methods for the preservation of nitrile hydration activity of cells containing a nitrile hydratase, where an aliphatic nitrile is enzymatically converted to an amide without subsequent conversion of the amide to the corresponding carboxylic acid ammonium salt, are described in U.S. Pat. Nos. 4,931,391 and 4,900,672. These methods for the stable preservation of nitrile hydratase activity of unimmobilized or immobilized microorganisms add at least one compound selected from the group consisting of nitrites, amides, or organic acids to a suspension of the unimmobilized or immobilized cells.

U.S. Pat. No. 4,343,900 describes a process to produce acrylamide from acrylonitrile using a microorganism having a nitrilasic activity (that is, a nitrile hydratase) which includes in the reaction mixture an alkali metal carbonate or bicarbonate. The alkali metal carbonate or bicarbonate is added to prevent a loss of enzyme activity that occurs due to a swelling of fixed cells during the reaction, and this loss of activity is not normally observed when physiological saline or phosphate buffer is added to the reaction mixture. In this same method, the addition of alkali metal carbonate or bicarbonate to reaction mixtures for the production of acrylamide from acrylonitrile is preferably done in combination with the addition of an organic carboxylic acid, thereby maintaining the enzymatic activity for a long period of time while acrylonitrile is converted to acrylamide.

The problems to be solved are to stabilize nitrilase activity and to reduce microbial contamination or putrefacation in suspensions of unimmobilized or immobilized cells. Different methods have been used to stabilize cells having either nitrile hydratase or nitrilase activity, where these two enzyme activities are produced by different types of enzymes which have different mechanisms for catalyzing nitrile hydrolysis to amides or acids, respectively. An examination of the effect of various carboxylic acid salts on the storage stability of nitrilase activity did not prevent the loss of nitrilase activity with time as was seen with nitrile hydratase. Similarly, the use of various inorganic salts previously disclosed as preserving the nitrilase or nitrile hydratase of microorganisms also did not stabilize the nitrilase activity of the microbial cells of the present invention upon storage as aqueous suspensions.

SUMMARY OF THE INVENTION

The invention solves the stated problem. It is a method for preserving microbial cells having nitrilase activity and for stabilizing the nitrilase activity thereof, the method comprising adding to an aqueous suspension of immobilized or unimmobilized microbial cells having nitrilase activity at least one compound selected from the group consisting of inorganic carbonate salts and inorganic bicarbonate salts wherein the resulting total concentration of the inorganic salts in the aqueous suspension ranges from 100 mM to the saturation concentration of the inorganic salts. The microbial cells having nitrilase activity are selected from the group consisting of Acidovorax facilis 72W (ATCC 55746), Acidovorax facilis 72-PF-15 (ATCC 55747) and Acidovorax facilis 72-PF-17 (ATCC 55745). The group of inorganic carbonate and bicarbonate salts are preferably selected from the group consisting of ammonium bicarbonate, sodium bicarbonate, and potassium bicarbonate. The conditions for the method include where the pH of the aqueous suspension of microbial cells having nitrilase activity is from about pH 6 to about pH 10 and the temperature of the aqueous suspension of microbial cells ranges from about 0° C. to about 45° C. The microbial cells are preferably immobilized in either polyacrylamide gel or carrageenan. In a preferred embodiment, the microbial cells are immobilized in carrageenan, the compound is ammonium bicarbonate, and the resulting total concentration of ammonium bicarbonate in the aqueous suspension ranges from about 100 mM to about 1000 mM. In another preferred embodiment of the method, the microbial cells are unimmobilized, the compound is sodium bicarbonate, and the resulting total concentration of ammonium bicarbonate in the aqueous suspension ranges from about 100 mM to about 1000 mM.

BRIEF DESCRIPTION OF THE BIOLOGICAL DEPOSITS

Applicants have made the following biological deposits under the terms of the Budapest Treaty:

| Depositor Identification Reference | Int'l. Depository Designation | Date of Deposit |
| --- | --- | --- |
| Acidovorax facilis 72-PF-17 | ATCC 55745 | 8 March 1996 |
| Acidovorax facilis 72W | ATCC 55746 | 8 March 1996 |
| Acidovorax facilis 72-PF-15 | ATCC 55747 | 8 March 1996 |

As used herein, "ATCC" refers to the American Type Culture Collection international depository located at 10801 University Boulevard, Manassas, Va. 20110-2209, U.S.A. The "ATCC No." is the accession number to cultures on deposit with the ATCC.

DETAILED DESCRIPTION OF THE INVENTION

A method for stabilizing the nitrilase activity of unimmobilized or immobilized microbial cells has been developed, wherein the cells are stored in an aqueous buffer containing from 0.100 M to the saturation concentration of at least one inorganic salt of bicarbonate or carbonate, including but not limited to ammonium, sodium and potassium salts of bicarbonate or carbonate. Storage solutions containing at least 100 mM bicarbonate or carbonate salt significantly limit microbial contamination or putrefaction of the stored enzyme catalyst, and also stabilize the desired nitrilase activity of the unimmobilized or immobilized cells. Microorganisms which are characterized by a nitrilase activity and are stably preserved by this method include but are not limited to Acidovorax facilis 72-PF-15 (ATCC 55747), Acidovorax facilis 72-PF-17 (ATCC 55745), and Acidovorax facilis 72W (ATCC 55746).

In this disclosure, a number or terms and abbreviations are used. The following definitions are provided.

"High pressure liquid chromatography" is abbreviated HPLC.

"Polyacrylamide gel" is abbreviated PAG.

The term "nitrilase" refers to an enzyme that can be used to directly convert a nitrile to the corresponding carboxylic acid in aqueous solution without the intermediate formation of an amide (R—CN+2H$_2$O→RCOOH+NH$_3$).

The term "stabilize" refers to maintaining the activity of an enzyme catalyst in whole unimmobilized or immobilized microbial cells such that there is no continuous loss of enzyme activity over time relative to the initial enzyme catalyst activity. The effect is to maintain enzyme activity at levels similar to those observed at Day 0 following preparation of the enzyme catalyst such that the useful life of the enzyme catalyst is prolonged.

The terms "preserve" or "preservation" refer to preventing or limiting putrefaction (microbial contamination or cell lysis) of nitrilase-containing microbial cells. The effect is to significantly limit contamination of the unimmobilized or immobilized cell aqueous suspension by maintaining cell integrity without lysis relative to cells not treated with this method.

U.S. Pat. Nos. 5,814,508 and 5,858,736 describe processes for the preparation of five-membered ring lactams or six-membered ring lactams from aliphatic α, ω-dinitriles, where an aliphatic α, ω-dinitrile is first converted to an ω-cyanocarboxylic acid ammonium salt in aqueous solution using microbial cells having an aliphatic nitrilase (EC 3.5.5.7) activity, followed by the direct conversion of the ammonium salt of the (ω-cyanocarboxylic acid to the corresponding lactam by hydrogenation in aqueous solution. In the course of preparing and storing unimmobilized or immobilized cells having nitrilase activity for this process as suspensions in aqueous solution containing, for example, phosphate buffer or physiological saline, it was found that many of these solutions did not prevent microbial contamination or putrefaction of the stored catalyst at temperatures ranging from approximately 5° C. to 30° C. In those cases where microbial contamination or putrefaction was not observed, a significant loss of nitrilase activity still occurred during storage. Freezing of immobilized cell catalysts typically resulted in the destruction of the immobilization matrix, and while unimmobilized cells could be stored frozen without significant loss of activity for months, a significant cost was associated with this method. Because storage of these microbial catalysts for weeks or months before use after preparation without loss of enzyme activity or putrefication is desirable, a method of stably preserving aqueous suspension of the unimmobilized or immobilized microbial cell catalysts in storage was sought.

An examination of the effect of various inorganic salts on the storage stability of the nitrilase activity of unimmobilized or immobilized Acidovorax facilis 72W (ATCC 55746), including some of those described in EP 0707061 for the stable preservation of the nitrilase activity of Gordona terrae MA-1, was conducted. Storage solutions containing potassium phosphate, ammonium sulfate, or ammonium chloride at various concentrations did not prevent the loss of nitrilase activity with time (see accompanying examples). Salts of organic acids such as acetate or propionate, previously reported to stabilize the nitrile hydratase activity of microbial cells, were also examined, even though the nitrile hydratase and nitrilase enzymes are different types of enzymes with different mechanisms for catalyzing nitrile hydrolysis to amides or acids, respectively. As disclosed in the accompanying examples, ammonium acetate or ammonium propionate were not effective in preserving the nitrilase activity of unimmobilized or immobilized Acidovorax facilis 72W cells.

It was discovered that carbonate and bicarbonate salts, including but not limited to ammonium bicarbonate, sodium bicarbonate, and potassium bicarbonate, are effective for both 1) preventing significant microbial contamination or putrefaction of suspensions of unimmobilized or immobilized cells containing nitrilase activity (specifically, *Acidovorax facilis* 72W cells), and 2) stabilizing the nitrilase activity of these suspensions, as evidenced by the results disclosed in the accompanying examples.

Organisms Potentially Expressing Nitrilase Genes

Many different genera are known to express nitrilase activity or contain genes which are thought to express nitrilase proteins. Both Gram negative (e.g. Comamonas, Acidovorax, Klebsiella [McBride et al., *Appl. Environ. Microbiol.* 52: 325–330 (1986)], Acinetobacter [Yamamoto et al., *Agric. Biol. Chem.* 55: 1459–1466 (1991)], Alcaligenes [Yamamoto et al., *J Ferm Bioeng* 73: 425–430 (1992)]) and Gram positive (e.g., Rhodococcus [Bhalla et al., *Acta Biotechnol* 15: 297–306 (1995)], Arthrobacter [Bandyopadhyay et al., *Appl. Environ. Microbiol.* 51: 302–306 (1986)], Gordona [DNA encoding novel nitrilase from Gordona terrae. NCBI GenBank ACCESSION E12616, Patent: JP1997037788-A 1 Feb. 10, 1997], Bacillus [Cramp et al., *Microbiol* 143: 2313–2320 (1997)]) bacteria expressing nitrilase activity are known. A number of reports are also known from plants (*Nicotiana tabacum* [Tsunoda, NCBI GenBank, ACC. #D83078], *Arabidopsis thaliana* [Zhou et al., *Plant Physiol.* 110, 1048 (1996)]), and fungi (e.g., *Fusarium solani* [Harper, *Brochem. J.* 167: 685–692 (1977b)]).

In higher organisms (Drosophila, Caenorhabditis, *Homo sapiens*), genes have been found that appear to code for nitrilase proteins [Pekarsky et al., *Proc. Nat'l. Acad. Sci. U.S.A.* 95 (15), 8744–8749 (1998)]. No discrete function has been reported for these genes. However, they retain high homology to known nitrilase genes and are expected to show typical nitrile hydrating activity. Nitrilase genes so far sequenced retain a common motif at the active site (Novo et al. (1995) FEBS Lett 367: 275–279) and thus are expected to be susceptible to preservation by the present invention.

Transformation and Expression of Nitrilase Genes

Heterologous expression of nitrilase activity from transformed hosts has been reported (Kobayashi et al. 1993, Proc. Nat. Acad. Sci. 90:247; Kobayashi et al. 1992. J. Biol. Chem. 267:20746; Kobayashi et al. 1992 Biochem. 31:9000–9007; U.S. Pat. No. 4,810,648). In some cases the hosts must be specifically modified in order to express good enzyme activity (Levy-Schil et al 1995. Gene 161:15–20; U.S. Pat. Nos. 5,830,693; 5,635,391). In cases where good nitrilase activity is found, the enzyme expressed by the transformed host retains the nitrile hydration activity of the native enzyme. It is anticipated that the present invention will preserve such nitrile hydration activity expressed by transformed hosts.

Strains

*Acidovorax facilis* 72W (ATCC 55746) was isolated from soil collected in Orange, Tex. Standard enrichment procedures were used with the following medium (E2 Basal Medium, pH 7.2):

| E2 Basal Medium | g/L |
|---|---|
| $KH_2PO_4$ | 1.4 |
| $NaH_2PO_4$ | 0.69 |
| Sodium citrate | 0.1 |
| $CaCl_2.2H_2O$ | 0.025 |
| KCl | 0.5 |
| NaCl | 1.0 |
| $MgSO_4.7H_2O$ | 0.5 |
| $FeSO_4.7H_2O$ | 0.05 |
| $CoCl_2.6H_2O$ | 0.01 |
| $MnCl_2.4H_2O$ | 0.001 |
| $ZnCl_2$ | 0.0005 |
| $NaMoO_4.2H_2O$ | 0.0025 |
| $NiCl_2.6H_2O$ | 0.01 |
| $CuSO_4.2H_2O$ | 0.005 |
| biotin | 0.0002 |
| folic acid | 0.0002 |
| pyridoxine.HCl | 0.001 |
| riboflavin | 0.0005 |
| thiamine.HCl | 0.00005 |
| nicotinic acid | 0.0005 |
| pantothenic acid | 0.0005 |
| vitamin $B_{12}$ | 0.00001 |
| p-aminobenzoic acid | 0.0005 |

The following supplementations were made to the E2 basal medium for the enrichments described above:

| Strain | Enrichment Nitrogen Source | Other Supplements |
|---|---|---|
| *A. facilis* 72 W | 0.2% (v/v) ethylsuccinonitrile | 0.3% (v/v) glycerol |

Strains were originally selected based on growth and ammonia production on the enrichment nitrile. Isolates were purified by repeated passing on Bacto® Brain Heart Infusion Agar (DIFCO, Detroit, Mich.) followed by screening for ammonia production from the enrichment nitrile. Purified strains were identified based on their carbon source utilization profile on a Biolog® test system (Hayward, Calif.) using Gram negative test plates.

Nitrilase Activity

For testing nitrilase activity, E2 basal medium with 10 g/L glucose was used to grow *Acidovorax facilis* 72W. The medium was supplemented with 25 mM (±)-2-methylglutaronitrile. A 10 mL volume of supplemented E2 medium was inoculated with 0.1 mL of frozen stock culture. Following overnight growth at room temperature (22–25° C.) on a shaker at 250 rpm, the 10 mL inoculum was added to 990 mL of fresh medium in a 2 L flask. The cells were grown overnight at room temperature with stirring at a rate high enough to cause bubble formation in the medium. Cells were harvested by centrifugation, washed once with 50 mM phosphate buffer (pH 7.2)/15% glycerol and the concentrated cell paste was immediately frozen on dry ice and stored at −65° C. Adiponitrile, 10 mM, was also used in the 1 liter fermentations. Fermentations were stopped after 16–20 hours of growth. The cell suspension was chilled to 4° C., harvested by centrifugation and frozen at −60° C. following one wash with 15% glycerol in 0.05 M phosphate buffer (pH 7.2).

Thawed cell pastes were used for testing nitrilase activity. The desired property of the microorganism is a nitrile hydrolyzing activity capable of regiospecific hydration of a dinitrile compound in the absence of interfering nitrile hydratase and amidase activities. Microorganisms tend to undergo mutation. Some mutations may be favorable to the desired nitrile conversion. Thus, even mutants of the native strain may be used to carry out the process of the instant invention.

The present invention is not limited to the particular organisms mentioned above, but includes the use of variants and mutants thereof that retain the desired property. Such variants and mutants can be produced from parent strains by various known means such as x-ray radiation, UV-radiation, and chemical mutagens.

Mutants of Acidovorax facilis 72W (ATCC 55746) with reduced capacity to produce the undesirable 2-methylglutaric acid by-product during hydrolysis of 2-methylglutaronitrile to 4-cyanopentanoic acid were selected based on their inability to use 2-methylglutaronitrile as a carbon and energy source. Specifically, an overnight culture of strain Acidovorax facilis 72W grown on LB/succinate medium (1% (w/v) Bacto-tryptone (DIFCO, Detroit, Mich.), 0.5% (w/v) Bacto-yeast extract (DIFCO), 1% (w/v) NaCl, 0.5% (w/v) sodium succinate hexahydrate) was exposed to 100 µg/mL solution of N-methyl-N'-nitro-N-nitrosoguanidine, a mutagenic agent, for approximately 30 minutes. This resulted in a 99.9% reduction in viable cells in the culture. Mutagenized cells were washed free of the mutagen by centrifugation in sterile, 1 M sodium phosphate buffer (pH 7.2). Washed cells were resuspended in LB/succinate medium and grown overnight at 30° C. Cells were then washed by centrifugation in sterile, 50 mM sodium phosphate buffer (pH 7.2) and resuspended in E2 minimal medium (without glucose) containing 0.2% (v/v) 2-methylglutaronitrile, and the antibiotics cycloserine, 0.2 mg/mL and piperacillin, 40 µg/mL. Cells were incubated overnight at 30° C. and again washed in sterile, 50 mM sodium phosphate buffer (pH 7.2). Washed cells were spread on agar plates containing a non-selective medium: E2 minimal medium (without glucose) plus 0.2% (v/v) 2-methylglutaronitrile and 0.5% (w/v) sodium succinate hexahydrate, at a concentration of 40–100 colony-forming units per plate. Plates were incubated for approximately 48 h at 30° C. to allow colonies to develop. Colonies which developed were replica plated onto agar plates containing selective medium: E2 minimal medium (without glucose) plus 0.2% (v/v) 2-methylglutaronitrile. Plates were incubated 48 h at 30° C. to allow colonies to develop. Mutants with desirable qualities do not grow well on the selective medium. Therefore, after 48 h, replicated plates were compared and strains showing growth only on non-selective medium were saved for further testing.

In total, approximately 5,120 colonies were checked from 89 plates and 19 strains with the desirable qualities were identified. These mutant strains were further tested for growth in liquid, E2 minimal medium (without glucose) plus 0.2% (v/v) 2-methylglutaronitrile. Strains which showed little or no growth in this medium were screened for their ability to produce 2-methylglutaric acid during growth in liquid medium consisting of E2 minimal medium (without glucose) plus 0.2% (v/v) 2-methylglutaronitrile and 0.5% (w/v) sodium succinate hexahydrate. As a result of this process, two mutant strains, identified as Acidovorax facilis 72-PF-15 (ATCC 55747) and Acidovorax facilis 72-PF17 (ATCC 55745) were chosen for further development due to their greatly diminished capacity to produce 2-methylglutaric acid.

To produce biocatalyst for stabilization studies, the following media can be used.

| Strain | Medium |
|---|---|
| 72-PF-15 | Lauria-Bertani Medium(Bacto ® tryptone, 10 g/L + Bacto ® yeast extract, 5 g/L + NaCl, 10 g/L) + 0.5% (w/v) sodium succinate.6H$_2$O |
| 72 W | E2 + 1% (w/v) glucose + 0.4% (w/v) adipamide |

To initiate growth, 10 mL of the appropriate medium was inoculated with 0.1 mL of frozen stock culture. Following overnight growth at 28° C. with shaking at 250 rpm, the growing cell suspension was transferred to 1 L of the same medium in a 2 L flask and growth continued at 28° C. with shaking. The 1 L growing cell suspension was then added to 9 L of the same medium in a 10 L fermentation vessel where growth continued. Nominal conditions in the fermenter were: ≧80% oxygen saturation, 25° C., pH 7.2 and 300–1000 rpm. After 20–91 hours, the vessel was chilled to 8–12° C. and cells harvested by centrifugation. The concentrated cell paste was immediately frozen on dry ice and stored at −70° C. until use. Numerous other supplementations which will serve as carbon and nitrogen sources for cell growth in E2 basal medium are known to those skilled in the art. These, as well as complex nutrient media, can be used to produce biocatalyst. The particular media described above should not be viewed as restrictive.

Cells having nitrilase activity and which are collected from culture broth for storage in cell suspensions, or for use in the preparation of immobilized cells which are subsequently stored in suspension, can be used directly without washing prior to storage or use in immobilization, or can be washed with the storage buffer prior to storage or immobilization. Cells may also be collected from culture broth and frozen prior to storage in cell suspensions or as suspensions of immobilized cells.

Nitrilase Assay

Nitrilase activity of unimmobilized cells was determined either by benzonitrile conversion to benzoic acid as measured spectrophotometrically by the increase in absorbance at 245 nm, or by 2-methyglutaronitrile conversion to 4-cyanopentanoic acid ammonium salt measured by HPLC. For the benzonitrile-based nitrilase assay, 5 mg frozen wet cell paste/mL was suspended in 0.1 M phosphate buffer (pH 7.0). Benzonitrile was added to a final concentration of 1 mM. The suspension was shaken at 250 rpm at 30° C. and samples were collected into a 4× volume of 0.04 M phosphoric acid stop solution at 0.5, 1, 2 and 4 minutes. After five minutes centrifugation at 15,800× g, the resulting supernatant was analyzed spectrophotometrically. Based on an empirically determined extinction coefficient for benzonitrile and benzoic acid in buffer plus stop solution, unit activity for the nitrilase was calculated by the following equation, where x is cell path length in centimeters (with correction for dilutions):

$$\Delta C(\text{Molar}) = \Delta O.D._{245}/1.81 \text{ Molar}^{-1}\text{cm}^{-1}(x)$$

For the 2-methylglutaronitrile-based assay, 1 mL of 50 mg dry cell weight/mL cell suspension (approximately 200 mg frozen cell paste/mL) in 0.100 M KH$_2$PO$_4$ (pH 7.0) buffer was added to 3.0 mL of 0.40 M 2-methylglutaronitrile in deionized water at 25° C. The reaction mixture was maintained at 25° C. with stirring, and 0.180 mL aliquots were removed and mixed with 5 µL of 6.0 N HCl and 20 µL of external standard solution (0.75 M N-methylpropionamide) in deionized water. The resulting mixture was immediately mixed, then centrifuged for 2 min at 12,000 rpm. The supernatant was analyzed by HPLC using a refractive index detector and a Supelcosil LC-18-DB column (25 cm×4.6 mm diameter), using an aqueous solvent containing 10 mM sodium acetate, 10 mM acetic acid and 7.5% methanol.

The nitrilase activity of immobilized cells was determined by mixing 16.5 g of an immobilized cells catalyst with 10.8 g of 2-methyglutaronitrile and 72.1 mL of 20 mM potassium phosphate buffer (pH 7.5) at 25° C. Aliquots (0.180 mL) were removed and mixed with 5 µL of 6.0 N HCl and 20 µL of external standard solution (0.75 M N-methylpropionamide) in deionized water. The resulting solution was immediately mixed, then centrifuged for 2 min at 12,000 rpm and the supernatant analyzed for 4-cyanopentanoic acid ammonium salt by HPLC as described above.

Immobilization

Nitrilase-containing cells can be immobilized using any of the methods and procedures known to those skilled in the art. These methods include, but are not limited to, immobilization in alginate, carrageenan, polyvinylalcohol, or polyacylamide gel, as well as immobilization by adsorption or attachment to ion exchange resins, diatomaceous earth (celite), activated carbon, silica, porous glass beads, alumina, zirconia, titania and the like.

Stabilization Compounds

The compound or compounds used in the present invention to stabilize nitrilase activity and preserve the integrity (prevent the microbial contamination or lysis) of unimmobilized or immobilized cells are selected from the group consisting of inorganic salts of carbonate or bicarbonate. Types of inorganic salts include, but are not limited to, sodium salts, potassium salts, and ammonium salts. A single compound selected from this group may be used as a nitrilase, stabilizer, or two or more compounds selected from this group may be included together in the preservative solution. Solutions containing carbonate or bicarbonate salts may additionally be prepared by sparging a buffered solution with carbon dioxide to generate the desired salt in situ, with appropriate pH adjustment. In the case of carrageenan-immobilized cells, ammonium or potassium salts are preferred, as these cations beneficially increase the degree of crosslinking in the carrageenan gel. In addition to stabilizing the nitrilase activity of unimmobilized or immobilized cells, the use of bicarbonate or carbonate salt additionally prevents the microbial contamination or putrefaction of suspensions of the unimmobilized or immobilized cells.

The concentration of the inorganic carbonate or bicarbonate salt(s) in the aqueous preservative solution may range from 0.10 M to the saturation concentration of said inorganic salts. The saturation concentration of each salt will vary with temperature and concentration, and for stabilizing immobilized catalyst is preferably in the range of from 0.25 M to 1.0 M. In the case of unimmobilized cells, it has been observed that at concentrations of bicarbonate salts equal to or greater than 0.50 M, the cell suspensions become heterogenous, although no loss of nitrilase activity is observed; therefore the preferable range of concentration of the inorganic salt for the stabilization of unimmobilized cells is from 0.10 M to 0.50 M.

The pH of the suspension is preferably from 5 to 10, with a more preferred pH range of from 6.5 to 8.0. The pH of the aqueous storage suspensions may be adjusted with a suitable acid, such as acetic, hydrochloric, sulfuric, or phosphoric acid, or a suitable base, such as ammonium hydroxide, sodium hydroxide, or potassium hydroxide.

The temperature at which the unimmobilized or immobilized cells are stably preserved in aqueous solutions containing one or more inorganic salts of bicarbonate or carbonate may range from approximately 0° C. (or just above the freezing point of the preservative solution) and 45° C., with a preferred range of from 5° C. to 30° C.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "h" means hour(s), "d" means day(s), "µL" means microliter(s), "mL" means milliliter(s), "L" means liter(s), "mM" means millimolar, "M" means molar, "mmol" means millimole(s).

Example 1

Storage Stability of Unimmobilized *Acidovorax facilis* Cell Nitrilase Activity

*Acidovorax facilis* 72W cells were isolated from cultured broth by centrifugation, and then suspended at a concentration of 1–5% dry cell weight in aqueous potassium phosphate (0.10 M or 1.00 M), sodium acetate (0.10 M or 1.00 M), or sodium bicarbonate (0.10 M or 0.30 M) at pH 7.3, and the resulting suspensions stored at 5° C. in capped glass bottles. Samples were removed from the cell suspensions over time and the samples assayed for nitrilase activity. Table 1 shows the relative nitrilase activity of the stored cell suspensions, with the nitrilase activity of the suspensions at day 0 defined as 100%. Cells stored for 92 days in 0.10 M or 0.30 M sodium bicarbonate retained a significantly-higher percentage of the initial nitrilase activity when compared to storage in either 0.10 M or 1.0 M sodium acetate or potassium phosphate.

TABLE 1

| | nitrilase activity (%) | | | | | |
|---|---|---|---|---|---|---|
| | KH$_2$PO$_4$ | | NaOAc | | NaHCO$_3$ | |
| Day | 0.10 M | 1.00 M | 0.10 M | 1.00 M | 0.10 M | 0.30 M |
| 0 | 100 | 100 | 100 | 100 | 100 | 100 |
| 39 | 93 | 86 | 87 | 82 | 97 | — |
| 41 | — | — | — | — | — | 106 |
| 64 | 96 | 86 | 72 | 82 | 104 | — |
| 69 | — | — | — | — | — | 92 |
| 92 | 81 | 78 | 63 | 76 | 95 | 95 |

Example 2

Immobilization of *Acidovorax facilis* 72W in Carrageenan Particles

*Acidovorax facilis* 72W wet cell paste (45 grams) was mixed with 45 mL of 0.88% NaCl, and the resulting suspension heated at 50° C. for 1 h to inactivate undesirable nitrile hydratase activity. The 50° C. cell suspension was then added to 135.0 g of a 5 wt % solution of Pronova ISAGEL RG300 carrageenan at 55° C. with mixing. The resulting suspension was then immediately gelled by cooling to 5° C. in an ice/water bath for 1 h. The resulting gel was cut into particles approximately 2 mm in diameter, and the immobilized cell particles then hardened in 450 mL of 0.30 M KCl, 20 mM KH$_2$PO$_4$ (adjusted to pH 7.0 with KOH) at 5° C. for 18 h. The hardening solution was then removed by washing the immobilized cell particles three times with 5 mM KCl, 20 mM KH$_2$PO$_4$ (pH 7.0) at 5° C.

Example 3

Immobilization of *Acidovorax facilis* 72W in Polyacrylamide Gel Particles

A solution of 13.8 g acrylamide and 1.20 g methylenebisacrylamide in 15.0 mL water at 25° C. was added with stirring to a suspension of 30.0 g (wet cell weight) *Acidovorax facilis* 72W in 82 mL of 0.10 M KH$_2$PO$_4$ (pH 7.0) at 10° C. with stirring. To the resulting mixture was added tetramethylethylenediamine (0.45 mL) and 7.5 mL of 5% (w/v) potassium persulfate at 25° C. The resulting polymerized gel was stored for 1 h at 10° C. in an ice bath, then cut into particles approximately 2 mm in diameter. The immobilized cell particles were wash twice with 50 mM KH$_2$PO$_4$ (pH 7.0) at 5° C.

Example 4

Storage Stability of Immobilized *Acidovorax facilis* Nitrilase Activity

*Acidovorax facilis* 72W cells (5% dry cell weight) were immobilized in Pronova ISAGEL RG300 carrageenan (3.0 wt %) as in Example 2 above and the resulting catalyst particles suspended in aqueous 1.0 M potassium phosphate, ammonium acetate, ammonium propionate, ammonium bicarbonate, or ammonium sulfate, or in 50 mM potassium phosphate containing 1.0 M ammonium chloride at pH 7.3. The resulting immobilized catalyst suspensions were stored at 5° C. in capped glass bottles, and samples were removed over time and the immobilized *Acidovorax facilis* 72W cells assayed for nitrilase activity.

Table 2 shows the relative nitrilase activity of the stored immobilized cell suspensions, with the activity at day 0 defined as 100%. Immobilized cells stored in 1.0 M ammonium bicarbonate retained a significantly-higher percentage of the initial nitrilase activity when compared to storage in 1.0 M potassium phosphate, ammonium acetate, ammonium propionate, or in 50 mM potassium phosphate containing 1.0 M ammonium chloride, at pH 7.3 and 5° C.

TABLE 2

| | nitrilase activity (%) | | | | | |
|---|---|---|---|---|---|---|
| Day | NH$_4$HCO$_3$ (1.0 M) | KH$_2$PO$_4$ (1.0 M) | NH$_4$OAc (1.0 M) | ammonium propionate (1.0 M) | NH$_4$CL (1.0 M) KH$_2$PO$_4$ (50 mM) | (NH$_4$)$_2$SO$_4$ (1.0 M) |
| 0 | 100 | 100 | 100 | 100 | 100 | 100 |
| 15 | — | — | — | — | — | 93 |
| 23 | 96 | 71 | 78 | 84 | 83 | — |
| 27 | — | — | — | — | — | 72 |
| 43 | — | 53 | — | 79 | — | — |
| 45 | 98 | — | 67 | — | — | — |
| 46 | — | — | — | — | 67 | — |
| 56 | 102 | — | 60 | — | — | — |
| 60 | — | — | — | — | 62 | — |
| 74 | — | — | — | 73 | — | — |
| 81 | 99 | — | 50 | — | — | — |
| 95 | — | — | 40 | — | — | — |
| 98 | 107 | — | — | 66 | — | — |

Example 5

Storage Stability of Immobilized *Acidovorax facilis* Nitrilase Activity

*Acidovorax facilis* 72W cells (5% dry cell weight) were immobilized in Pronova ISAGEL RG300 carrageenan (3.0 wt %) as in Example 2 above and the resulting catalyst particles suspended in aqueous 1.0 M ammonium bicarbonate at pH 7.3. The resulting immobilized catalyst suspension was stored at 25° C. in a capped glass bottle, and samples were removed over time and the immobilized *Acidovorax facilis* 72W cells assayed for nitrilase activity.

Table 3 shows the relative nitrilase activity of the stored immobilized cell suspension, with the activity at day 0 defined as 100%.

TABLE 3

| day | nitrilase activity (%) NH₄HCO₃ |
|---|---|
| 0 | 100 |
| 10 | 94 |
| 23 | 94 |
| 38 | 92 |
| 59 | 93 |
| 78 | 88 |
| 105 | 91 |

Example 6

Microbial Contamination in Suspensions of Immobilized *Acidovorax facilis*

*Acidovorax facilis* 72W cells (5% dry cell weight) were immobilized in Pronova ISAGEL RG300 carrageenan (3.0 wt %) as in Example 2 above or in polyacrylamide gel (PAG, 10 wt %) as in Example 3 above, and the resulting catalyst particles suspended in aqueous solutions containing: a) 50 mM potassium phosphate (pH 7.0); b) 1.0 M ammonium acetate (pH 7.3); c) 1.0 M ammonium bicarbonate (pH 7.3); or d) 50 mM potassium phosphate/1.0 M ammonium chloride (pH 7.0). The resulting immobilized catalyst suspensions were stored at 5° C. in capped glass bottles, and samples of the storage solution were removed over time. The samples were examined for microbial contamination by measurement of the change in optical density (OD) at 600 nm.

Example 4, Table 2, shows that immobilized cells stored in 1.0 M ammonium bicarbonate retained a significantly-higher percentage of the initial nitrilase activity when compared to storage in 1.0 M potassium phosphate, ammonium acetate, ammonium propionate, or in 50 mM potassium phosphate containing 1.0 M ammonium chloride, at 5° C. Microbial contamination, indicated by an increase in the measured optical density (OD) of the storage buffer over time, occurred with cells immobilized in either PAG or RG300 carrageenan when stored in 50 mM potassium phosphate (Table 4), while no significant microbial contamination or putrefaction, was observed for cells stored in 1.0 M ammonium acetate, ammonium bicarbonate, or 1.0 M ammonium chloride/50 mM potassium phosphate. Of the three storage suspensions which showed no microbial contamination or putrefaction; only the immobilized cells stored in 1.0 M ammonium bicarbonate showed no significant loss of nitrilase activity (see Example 4, Table 2).

TABLE 4

| | OD (600 nm) | | | | |
|---|---|---|---|---|---|
| Day | PAG, KH₂PO₄ (50 mM) | RG300, KH₂PO₄ (50 mM) | RG300, NH₄OAc (1.0 M) | RG300, NH₄OAc (1.0 M) | RG300, NH₄Cl (1.0 M) KH₂PO₄ (50 mM) |
| 1 | — | 0.026 | 0.055 | 0.045 | 0.054 |
| 2 | 0.061 | — | — | — | — |
| 5 | 0.047 | 0.075 | — | — | 0.035 |
| 8 | 0.079 | 0.137 | — | — | 0.017 |
| 11 | 0.207 | — | — | — | — |
| 12 | — | 0.115 | 0.008 | 0.001 | 0.040 |
| 15 | 0.360 | — | — | — | — |
| 16 | — | 0.276 | — | — | 0.067 |
| 18 | 0.419 | — | — | — | — |
| 19 | — | 0.221 | — | — | 0.033 |
| 23 | — | 0.521 | — | — | 0.050 |
| 26 | — | — | 0.029 | 0.073 | — |
| 33 | — | — | 0.027 | 0.082 | — |
| 46 | — | — | 0.048 | 0.104 | — |
| 47 | — | — | — | — | 0.032 |
| 57 | — | — | 0.085 | 0.072 | — |
| 61 | — | — | — | — | 0.033 |

What is claimed is:

1. A method for preserving immobilized or unimmobilized microbial cells having nitrilase activity and for stabilizing the nitrilase activity thereof, the method comprising:

adding to an aqueous suspension of immobilized or unimmobilized microbial cells having nitrilase activity at least one compound selected from the group consisting of inorganic carbonate salts and inorganic bicarbonate salts wherein the resulting total concentration of the inorganic salts in the aqueous suspension ranges from 100 mM to the saturation concentration of the inorganic salts.

2. The method of claim 1 wherein the microbial cells having nitrilase activity are selected from the group consisting of *Acidovorax facilis* 72W (ATCC 55746), *Acidovorax facilis* 72-PF-15 (ATCC 55747), and *Acidovorax facilis* 72-PF-17 (ATCC 55745).

3. The method of claim 1, wherein the compound is selected from the group of inorganic bicarbonate salts consisting of ammonium bicarbonate, sodium bicarbonate, and potassium bicarbonate.

4. The method of claim 1, wherein the pH of the aqueous suspension of immobilized or unimmobilized microbial cells having nitrilase activity is from about pH 6 to about pH 10.

5. The method of claim 1 wherein the temperature of the aqueous suspension of immobilized or unimmobilized microbial cells ranges from about 0° C. to about 45° C.

6. The method of claim 1 wherein the microbial cells are immobilized in either polyacrylamide gel or carrageenan.

7. The method of claim 6 wherein the microbial cells are immobilized in carrageenan, the compound is ammonium bicarbonate, and the resulting total concentration of ammonium bicarbonate in the aqueous suspension ranges from about 100 mM to about 1000 mM.

8. The method of claim 1 wherein the microbial cells are unimmobilized, the compound is sodium bicarbonate, and the resulting total concentration of sodium bicarbonate in the aqueous suspension ranges from about 100 mM to about 1000 mM.

* * * * *